(12) United States Patent
Kraemer

(10) Patent No.: US 10,945,855 B2
(45) Date of Patent: Mar. 16, 2021

(54) SPINAL FUSION APPARATUS

(71) Applicant: Paul E. Kraemer, Westfield, IN (US)

(72) Inventor: Paul E. Kraemer, Westfield, IN (US)

( * ) Notice: Subject to any disclaimer, the term of this patent is extended or adjusted under 35 U.S.C. 154(b) by 210 days.

(21) Appl. No.: 15/502,867

(22) PCT Filed: Aug. 12, 2015

(86) PCT No.: PCT/US2015/044879
§ 371 (c)(1),
(2) Date: Feb. 9, 2017

(87) PCT Pub. No.: WO2016/025612
PCT Pub. Date: Feb. 18, 2016

(65) Prior Publication Data
US 2017/0231781 A1 Aug. 17, 2017

Related U.S. Application Data

(60) Provisional application No. 62/036,263, filed on Aug. 12, 2014, provisional application No. 62/045,958, filed on Sep. 4, 2014, provisional application No. 62/102,911, filed on Jan. 13, 2015, provisional application No. 62/105,833, filed on Jan. 21, 2015.

(51) Int. Cl.
A61F 2/44 (2006.01)
A61F 2/30 (2006.01)

(52) U.S. Cl.
CPC .......... *A61F 2/4455* (2013.01); *A61F 2/4425* (2013.01); *A61F 2002/3054* (2013.01);
(Continued)

(58) Field of Classification Search
CPC .............. A61F 2/4455; A61F 2/4425; A61F 2002/30471; A61F 2002/30489;
(Continued)

(56) References Cited

U.S. PATENT DOCUMENTS 5,782,832 A 7/1998 Larsen et al.
6,685,742 B1 2/2004 Jackson
(Continued)

OTHER PUBLICATIONS

International Search Report and Written Opinion for PCT/US2015/044879, dated Jan. 7, 2016.
(Continued)

*Primary Examiner* — Eduardo C Robert
*Assistant Examiner* — David C Comstock
(74) *Attorney, Agent, or Firm* — Wiley Rein LLP

(57) ABSTRACT

An interbody spinal fusion cage for posterior interbody fusion procedures includes a superior member and an inferior member connected to each other via a joint. The joint allows the interbody spinal fusion cage to achieve lordosis even if implanted non-orthogonal to the sagittal plane. For example, the joint can be a hinge oriented non-normal to a longitudinal axis of the interbody spinal fusion cage, a polyaxial ball joint, and/or a universal joint. Complementary locking mechanisms, such as locking teeth or a ratchet-and-pawl arrangement, can be provided near the posterior ends of the superior and inferior members in order to prohibit the posterior ends of the superior and inferior members from separating from each other in situ. Bone holes can be provided in the superior and inferior members.

10 Claims, 11 Drawing Sheets

(52) U.S. Cl.
CPC ............... *A61F 2002/30471* (2013.01); *A61F 2002/30476* (2013.01); *A61F 2002/30477* (2013.01); *A61F 2002/30487* (2013.01); *A61F 2002/30518* (2013.01); *A61F 2002/30522* (2013.01); *A61F 2002/30528* (2013.01); *A61F 2002/30538* (2013.01); *A61F 2002/30649* (2013.01); *A61F 2002/30772* (2013.01)

(58) Field of Classification Search
CPC .. A61F 2002/30518; A61F 2002/30522; A61F 2002/30528; A61F 2002/3054; A61F 2002/30649; A61F 2002/30772
USPC ............ 623/17.14, 17.15; 606/246–249, 279
See application file for complete search history.

(56) References Cited

U.S. PATENT DOCUMENTS

| | | | |
|---|---|---|---|
| 7,204,853 B2 | 4/2007 | Gordon et al. | |
| D626,233 S * | 10/2010 | Cipoletti | A61F 2/447 D24/155 |
| 8,303,658 B2 | 11/2012 | Peterman | |
| 8,882,841 B2 | 11/2014 | Falahee | |
| 8,900,312 B2 | 12/2014 | McLean et al. | |
| 9,622,786 B2 * | 4/2017 | Arnin | A61B 17/7001 |
| 2004/0044411 A1 | 3/2004 | Suddaby | |
| 2004/0106998 A1 * | 6/2004 | Ferree | A61F 2/4425 623/17.16 |
| 2008/0119933 A1 | 5/2008 | Aebi et al. | |
| 2008/0133013 A1 * | 6/2008 | Duggal | A61F 2/4425 623/17.16 |
| 2011/0093077 A1 | 4/2011 | Aebi et al. | |
| 2011/0112644 A1 * | 5/2011 | Zilberstein | A61B 17/7079 623/17.15 |
| 2013/0158664 A1 | 6/2013 | Palmatier et al. | |
| 2014/0343678 A1 | 11/2014 | Suddaby et al. | |
| 2016/0022438 A1 * | 1/2016 | Lamborne | A61F 2/447 623/17.16 |

OTHER PUBLICATIONS

International Search Report and Written Opinion for PCT/US2017/018460, dated May 1, 2017.

* cited by examiner

SPINAL FUSION APPARATUS

CROSS-REFERENCE TO RELATED APPLICATIONS

This application claims the benefit of U.S. provisional application Nos. 62/036,263, filed 12 Aug. 2014; 62/045,958, filed 4 Sep. 2014; 62/102,911, filed 13 Jan. 2015; and 62/105,833, filed 21 Jan. 2015. Each of the foregoing provisional applications is hereby incorporated by reference as though fully set forth herein.

BACKGROUND

The instant disclosure relates to orthopedic surgery and neurosurgery. In particular, the instant disclosure relates to devices and methods for posterior interbody fusion procedures, including, without limitation, transforaminal lumbar interbody fusion ("TLIF") and posterior lumbar interbody fusion ("PLIF") procedures.

Sagittal balance and spinopelvic harmony have become prevalent concepts in spinal deformity over the past several years. Although there is no clear consensus, these concepts also apply to degenerative spinal surgery. Indeed, in many practices, spinal deformities often result from previous spinal operations where inadequate lordosis was achieved. Techniques such as anterior-posterior fusions and posterior alone operations can be predisposed to flatback deformities, in part because of the inability to control anterior and posterior columns simultaneously. Growing literature links these concepts to increases in adjacent segment stresses, degeneration, and revision operations, with attendant patient suffering and costs to the health care system.

Flatback deformity can lead to increased back pain, accelerated adjacent level changes, and repeat surgery. Fixing the problem in severe cases can involve three column osteotomy. Moderate cases can be treated, and initial deformity often prevented, with less osteotomies (e.g., Smith Peterson or Ponte osteotomoies), often with a coexistent transforaminal lumber interbody fusion ("TLIF") procedure. Indeed, TLIF alone, or TLIF in conjunction with posterior column osteotomies, is known to help prevent post-operative sagittal deformity.

One of the challenges attendant to a TLIF procedure is obtaining optimum increase in the height of the anterior column while achieving adequate posterior disc shortening. One component of this is anterior discal release, which is technique dependent, while maintaining height, which can be implant dependent. Another component is removing tissue to allow compression across the posterior disc, which is technique dependent, while preventing an implant from blocking full collapse/compression, which is implant dependent. Taken together, one can achieve maximum lordosis at an individual level from a posterior approach.

Numerous implants attempt to solve the problem of achieving optimum lordosis (e.g., up to about 30 degrees per level, as necessary and determined by the Pelvic incidence–9=lumbar lordosis formula). For example, U.S. Pat. No. 6,685,742 to Jackson teaches an articulated modular spinal fusion cage for implantation in the intervertebral space. Jackson's device, however, requires a more complex, and therefore more invasive, anterior approach. Moreover, Jackson's implant is not freely mobile; to change the amount of lordosis, the practitioner must manipulate a screw, again from an anterior approach; Jackson's device is not operable without the screw. In addition, Jackson's implant is limited to an orthogonal axis of lordosis (e.g., it can only achieve lordosis about an axis that is perpendicular to the long axis of the implant).

A number of extant devices (see, e.g., U.S. Pat. Nos. 8,900,312 and 8,900,313 to McLean et al. and Barreiro et al., respectively), seek to achieve increased lordosis by increasing the height of the device in situ. Such devices can, however, result in increased disc height without increased lordosis, potentially due to the blocking of the posterior aspect of the vertebral body.

Other device designs, such as disclosed in U.S. Pat. No. 8,882,841 to Falahee, seek to more adequately place the device in an ideal position anteriorly through steerable cages. These devices can be hindered by a learning curve, a lack of ideal bone graft placement, the requirement for a very complete discectomy, and diminished lordosis (relative to pre-procedure) if the device does not track as desired.

Still other extant devices increase height through the use of a tapered cage in one plane, inserted on its side and then rotated 90 degrees along its long axis, with the taper resulting in lordosis. Such devices, however, result in point loading during rotation (e.g., when at 45 degrees), which can cause damage to the soft endplate bone and ultimate cavitation of the bone around the graft. Moreover, posterior closure to increase lordosis can be blocked by the height of the posterior-most portion of the implant, which prevents the posterior aspect from collapsing.

BRIEF SUMMARY

It would therefore be desirable to provide an implant, such as for use in TLIF procedures, that maximizes anterior height (e.g., that maximizes the height of the anterior-most portion of the vertebral body, the anterior column), minimizes posterior height (e.g., that minimizes the height of the posterior-most portion of the vertebral body, the middle column), avoids point loading during insertion, inserts with minimal risk of neurologic trauma or damage to end plate bone, facilitates a posterior approach, achieves lordosis (e.g., up to about 30 degrees) even absent ideal placement and/or about non-orthogonal axes, and freely allows lordosis to increase after implantation and until the vertebral segment is ultimately fixed in place, usually through posterior instrumentation (e.g., pedicle screw/rod systems).

Disclosed herein is an interbody spinal fusion cage configured to achieve lordosis when placed posteriorly. The interbody spinal fusion cage includes: a superior member including an anterior end, a posterior end, and a superior bearing surface extending along an axis between the anterior end of the superior member and the posterior end of the superior member; an inferior member including an anterior end, a posterior end, and an inferior bearing surface extending along an axis between the anterior end of the inferior member and the posterior end of the inferior member; and a joint connected to the superior member at a first point between the anterior end of the superior member and the posterior end of the superior member and to the inferior member at a second point between the anterior end of the inferior member and the posterior end of the inferior member. The joint is oriented non-normal to the long axis of the superior member and the long axis of the inferior member. For example, the joint can form an angle between 50 degrees and 80 degrees with respect to the long axis of the superior member and the long axis of the inferior member (i.e., between about 10 degrees and about 40 degrees relative to the short axis of the interbody spinal fusion cage).

The superior member can include a superior bone hole through the superior bearing surface and the inferior member can include an inferior bone hole through the inferior bearing surface. In aspects of the disclosure, the superior bone hole is located anterior of the first point and the inferior bone hole is located anterior of the second point.

In some embodiments, the joint includes a ratchet and pawl. In additional embodiments, the joint includes a hinge. In still other embodiments, the joint includes a universal joint.

According to additional aspects of the disclosure, the superior member includes a first ratchet element posterior of the first point, the inferior member includes a second ratchet element posterior of the second point, and the first ratchet element and the second ratchet element are configured to allow the posterior end of the superior member and the posterior end of the inferior member to move towards each other and to prevent the posterior end of the superior member and the posterior end of the inferior member from moving apart from each other. It is also contemplated that the superior member can include a third ratchet element posterior of the first point, the first ratchet element and the third ratchet elements being on opposing sides of the axis of the superior member, the inferior member can include a fourth ratchet element posterior of the second point, the second ratchet element and the fourth ratchet element being on opposing sides of the axis of the inferior member, and the third ratchet element and the fourth ratchet element can be configured to allow the posterior end of the superior member and the posterior end of the inferior member to move towards each other and to prevent the posterior end of the superior member and the posterior end of the inferior member from moving apart from each other.

Also disclosed herein is an interbody spinal fusion cage configured to achieve lordosis when placed posteriorly, including: a superior member including an anterior end, a posterior end, a superior bearing surface extending between the anterior end of the superior member and the posterior end of the superior member, and a superior joint component between the anterior end of the superior member and the posterior end of the superior member; and an inferior member including an anterior end, a posterior end, an inferior bearing surface extending between the anterior end of the inferior member and the posterior end of the inferior member, and an inferior joint component between the anterior end of the inferior member and the posterior end of the inferior member, wherein the superior joint component is attached to the inferior joint component in a manner that allows the interbody spinal fusion cage to achieve lordosis even if implanted non-orthogonal to the sagittal plane.

The superior joint component can include a first hinge component and the inferior joint component can include a second hinge component, wherein the first and second hinge components together form a hinge that is non-normal to a longitudinal axis of the interbody spinal fusion cage.

In other embodiments, one of the superior joint component and the inferior joint component can include a ball and the other of the superior joint component and the inferior joint component can include a socket, and wherein the ball and socket together form a polyaxial ball and socket joint.

In still other embodiments disclosed herein, the superior joint component can include a first universal joint component and the inferior joint component can include a second universal joint component, and wherein the first and second universal joint components together form a universal joint.

According to aspects of the disclosure, the superior member can include first locking teeth proximate the posterior end of the superior member, the inferior member can include second locking teeth proximate the posterior end of the inferior member, and the first locking teeth can be configured to engage the second locking teeth in a manner that prohibits the posterior end of the superior member from separating from the posterior end of the inferior member. For example, one of the first locking teeth and the second locking teeth can include a ratchet and the other of the first locking teeth and the second locking teeth can include a pawl.

It is also contemplated that the superior member can include a superior bone hole through the superior bearing surface anterior of the superior joint component, and the inferior member can include an inferior bone hole through the inferior bearing surface anterior of the inferior joint component.

According to additional aspects of the disclosure, a method of performing a transforaminal lumbar interbody fusion includes: inserting, via a posterior approach, an interbody spinal fusion cage between two vertebrae, the interbody spinal fusion cage including: a superior member including an anterior end, a posterior end, and a superior bearing surface extending between the anterior end of the superior member and the posterior end of the superior member; an inferior member including an anterior end, a posterior end, and an inferior bearing surface extending between the anterior end of the inferior member and the posterior end of the inferior member; and a joint connecting the superior member to the inferior member in a manner that permits at least seesaw motion between the superior member and the inferior member; and securing the posterior end of the superior member to the posterior end of the inferior member in a lordotic configuration.

The joint permits at least seesaw motion between the superior member and the inferior member about an axis that is non-normal to a longitudinal axis of the interbody spinal fusion cage. For example, the joint can include a universal joint.

Securing the posterior end of the superior member to the posterior end of the inferior member can include securing the posterior end of the superior member to the posterior end of the inferior member using a ratchet lock, similar to that found in a zip tie.

The foregoing and other aspects, features, details, utilities, and advantages of the present invention will be apparent from reading the following description and claims, and from reviewing the accompanying drawings.

BRIEF DESCRIPTION OF THE DRAWINGS

In FIG. 3A, the superior and inferior members are separated to show details of the locking teeth thereon. In FIG. 3B, the locking teeth are engaged without appreciable lateral bending. In FIG. 3C, only one set of locking teeth are engaged as a result of lateral bending.

DETAILED DESCRIPTION

Figure 1A:
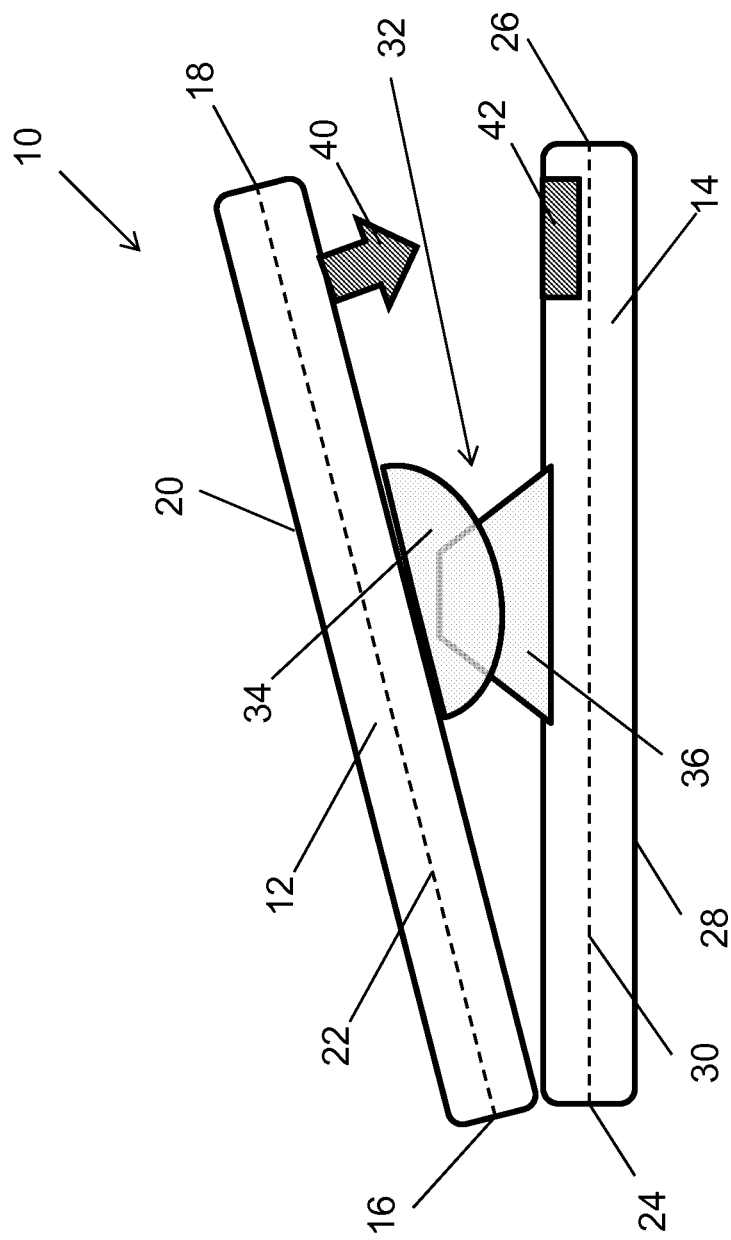
FIG. 1A is a side view schematic depiction of an interbody spinal fusion cage according to aspects of the instant disclosure, with the superior and inferior members configured for insertion into an interbody space.

FIG. 1 is a schematic side view of an interbody spinal fusion cage 10 according to aspects of the instant disclosure. As will be discussed in detail below, interbody spinal fusion cage 10 is configured such that it will achieve lordosis when placed between two vertebrae via a posterior approach.

Interbody spinal fusion cage 10 includes a superior member 12 and an inferior member 14. Superior member 12 includes an anterior end 16, a posterior end 18, and a superior bearing surface 20 that extends along an axis 22 (shown in dashed line) between anterior end 16 and posterior end 18. Similarly, inferior member 14 includes an anterior end 24, a posterior end 26, and an inferior bearing surface 28 that extends along an axis 30 (shown in dashed line) between anterior end 24 and posterior end 26.

Superior member 12 and anterior member 14 are interconnected via a joint 32. As illustrated to good advantage in FIG. 1, joint 32 is connected to superior member 12 at a first point between anterior end 16 and posterior end 18 and to inferior member 14 at a second point between anterior end 24 and posterior end 26. FIG. 1 shows these points of connection as approximately halfway between anterior ends 16, 24 and posterior ends 24, 26. It should be understood, however, that the points of connection can be more anterior or more posterior without departing from the spirit and scope of the instant teachings.

It is, however, desirable for the point of connection between joint 32 and superior member 12 to be at about the same level as the point of connection between joint 32 and inferior member 14. For example, if the point of attachment between joint 32 and superior member 12 is about 8 mm from posterior end 18, the point of attachment between joint 32 and inferior member 14 should also be about 8 mm from posterior end 26. Put another way, posterior ends 18 and 26 should be at about the same length from joint 32, so that neither of superior member and inferior member 12, 14 substantially overhangs the other.

Figure 1B:
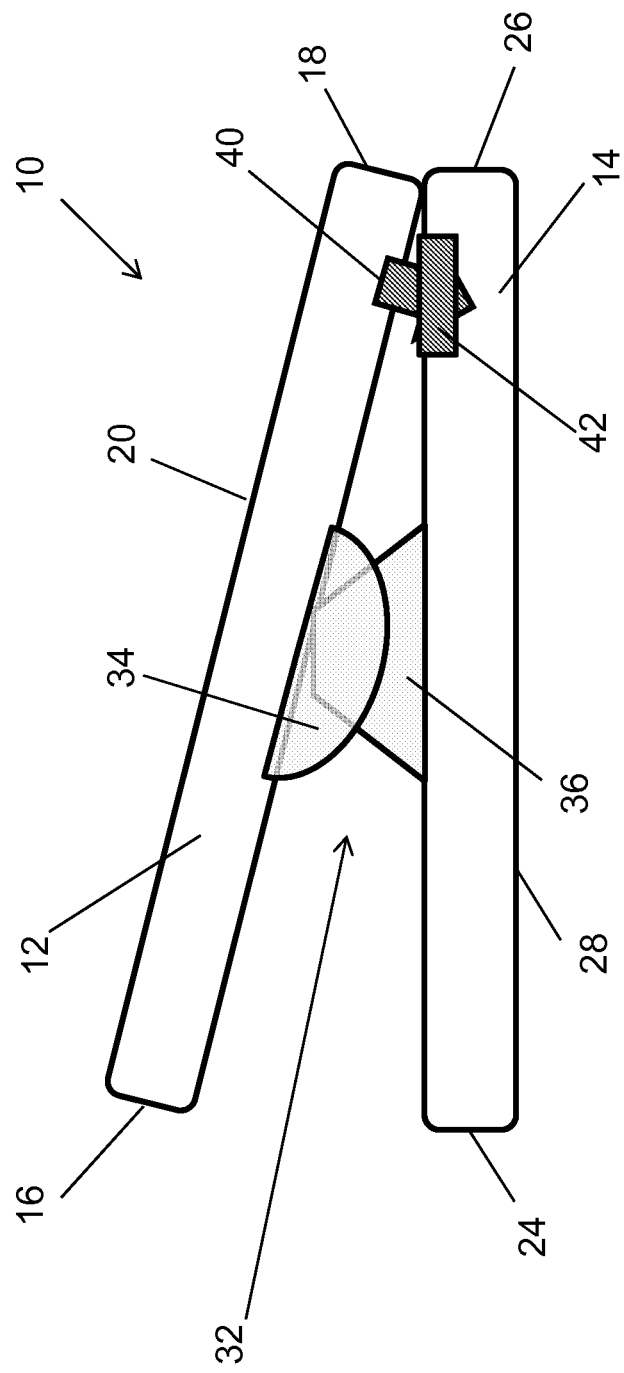
FIG. 1B is a side view schematic depiction of the interbody spinal fusion cage of FIG. 1A, with the superior and inferior members secured to one another after insertion into an interbody space.

FIGS. 1A and 1B illustrates that joint 32 generally includes a superior joint component 34 that is attached to superior member 12 and an inferior joint component 36 that is attached to inferior member 14. In embodiments, superior joint component 34 is fixedly attached to or integrally formed with superior member 12 and inferior joint component 36 is similarly fixedly attached to or integrally formed with inferior member 14. (As used herein, elements are "fixedly" attached to one another if they cannot be separated without the application of destructive force; in other words, elements that are "fixedly" interconnected are to be contrasted with those that are "releasably" or "removably" interconnected.) Likewise, joint components 34, 36 are desirably fixedly attached to one another, such that they cannot separate in situ. It is contemplated, however, that, in certain embodiments disclosed herein, joint 32 may be releasably or removably connected to either or both of superior member 12 and inferior member 14 and/or joint components 34, 36 may be releasably or removably connected to each other.

Joint 32 permits superior member 12 to move relative to inferior member 14. In particular, joint 32 (e.g., the interaction between superior joint component 34 and inferior joint component 36) facilitates movement between superior member 12 and inferior member 14 in a manner that allows interbody spinal fusion cage 10 to achieve lordosis even if implanted non-orthogonal to the sagittal plane.

Figure 2:
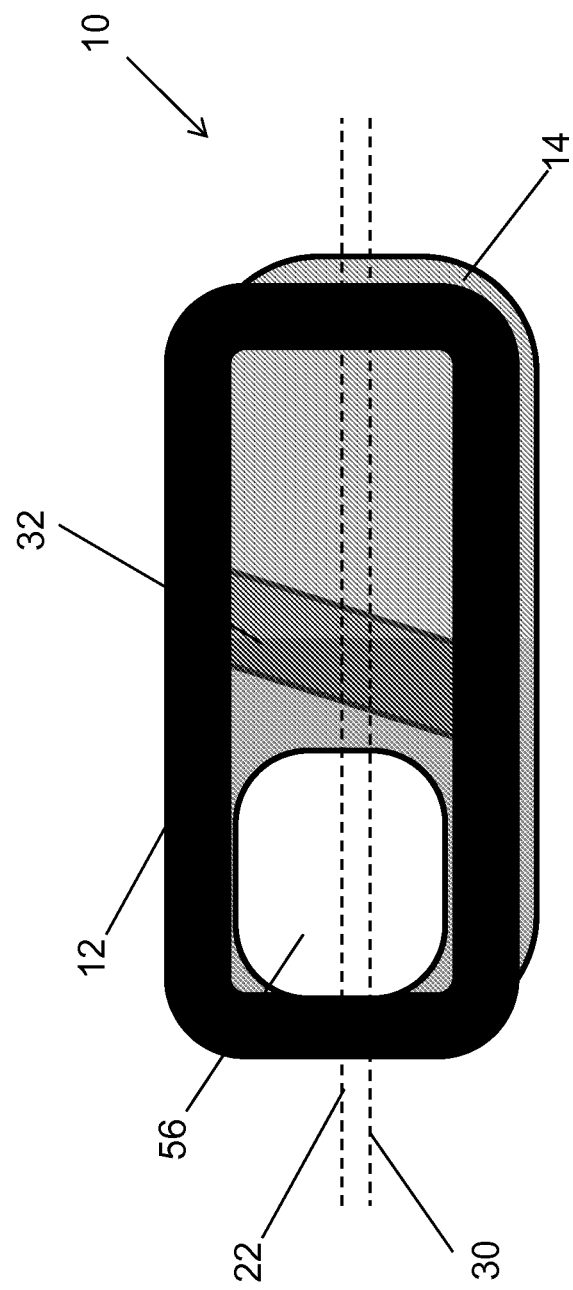
FIG. 2 is a top view schematic depiction of an interbody spinal fusion cage according to aspects of the instant disclosure.

As illustrated in FIG. 2, according to aspects of the instant disclosure, joint 32 is a hinge oriented non-normal to the longitudinal axis of interbody spinal fusion cage 10 (e.g., non-normal to axes 22 and 30, which are again shown in dashed line in FIG. 2). In aspects of the instant disclosure, the angle formed between hinge joint 32 and the longitudinal axis of interbody spinal fusion cage 10 is between about 50 degrees and about 80 degrees. Put another way, hinge joint 32 is about 10 degrees to about 40 degrees from normal to the longitudinal axis of interbody spinal fusion cage 10. As those of ordinary skill in the art will appreciate from the instant disclosure, hinge joint 32 permits superior member 12 and inferior member 14 to seesaw about the axis of hinge joint 32.

Figure 3A:
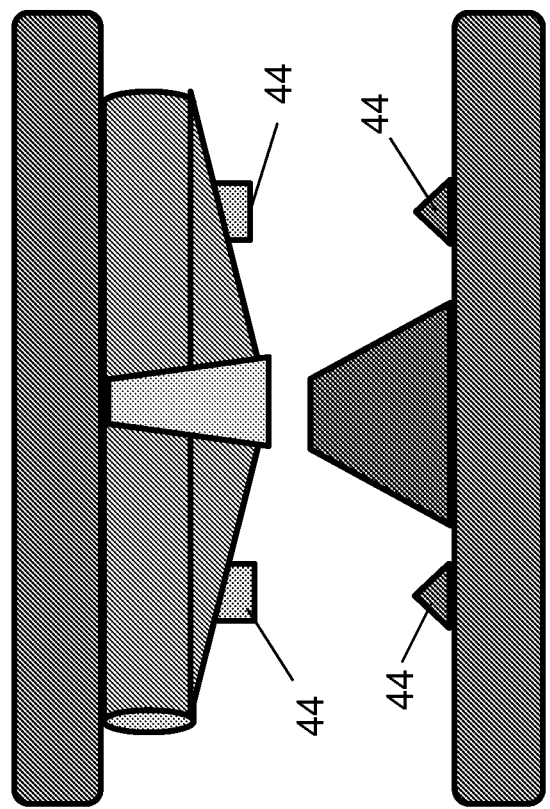
FIGS. 3A-3C are anterior-looking schematic views of an interbody spinal fusion cage according to aspects of the instant disclosure.
Figure 3B:
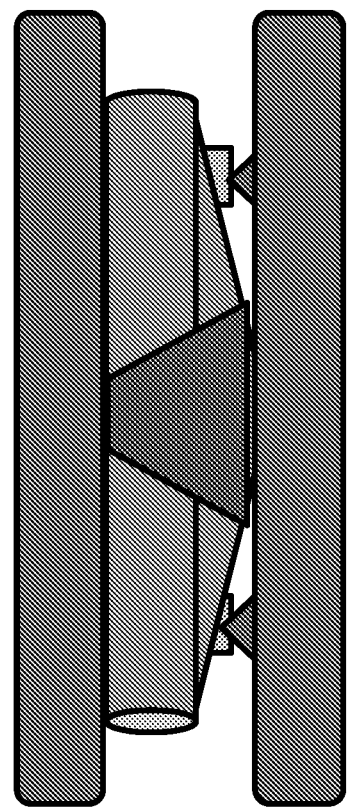
Figure 3C:
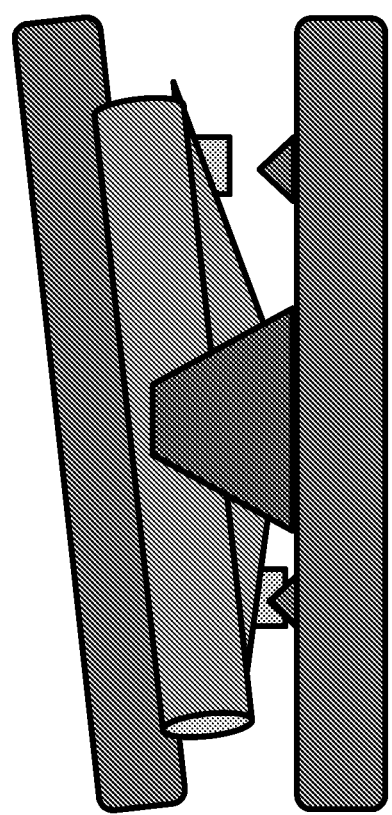

In other embodiments, joint 32 can be implemented as a universal joint. This is illustrated schematically in FIGS. 3A-3C. When seen from the top, the universal joint can also be oriented non-normal to the longitudinal axis of interbody spinal fusion cage 10 (and thus resemble the configuration schematically depicted in FIG. 2). The schematic end view of FIGS. 3A-3C illustrate that, in addition to allowing for flexion and extension, a universal joint advantageously allows for lateral bending in the spine.

Figure 4:
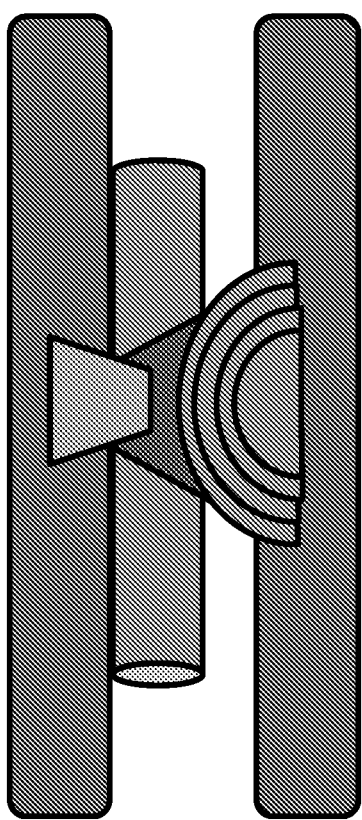
FIG. 4 is an anterior-looking cross-sectional schematic view of an interbody spinal fusion cage according to aspects of the instant disclosure, including a schematic depiction of a polyaxial ball joint.

In still other embodiments, joint 32 can be implemented as a polyaxial ball and socket joint. This configuration, which is schematically depicted in FIG. 4, also advantageously allows flexion, extension, and lateral bending.

Use of interbody spinal fusion cage 10 is illustrated in FIGS. 5A-5D. FIGS. 5A-5D are oriented with the posterior to the right.

Figure 5A:
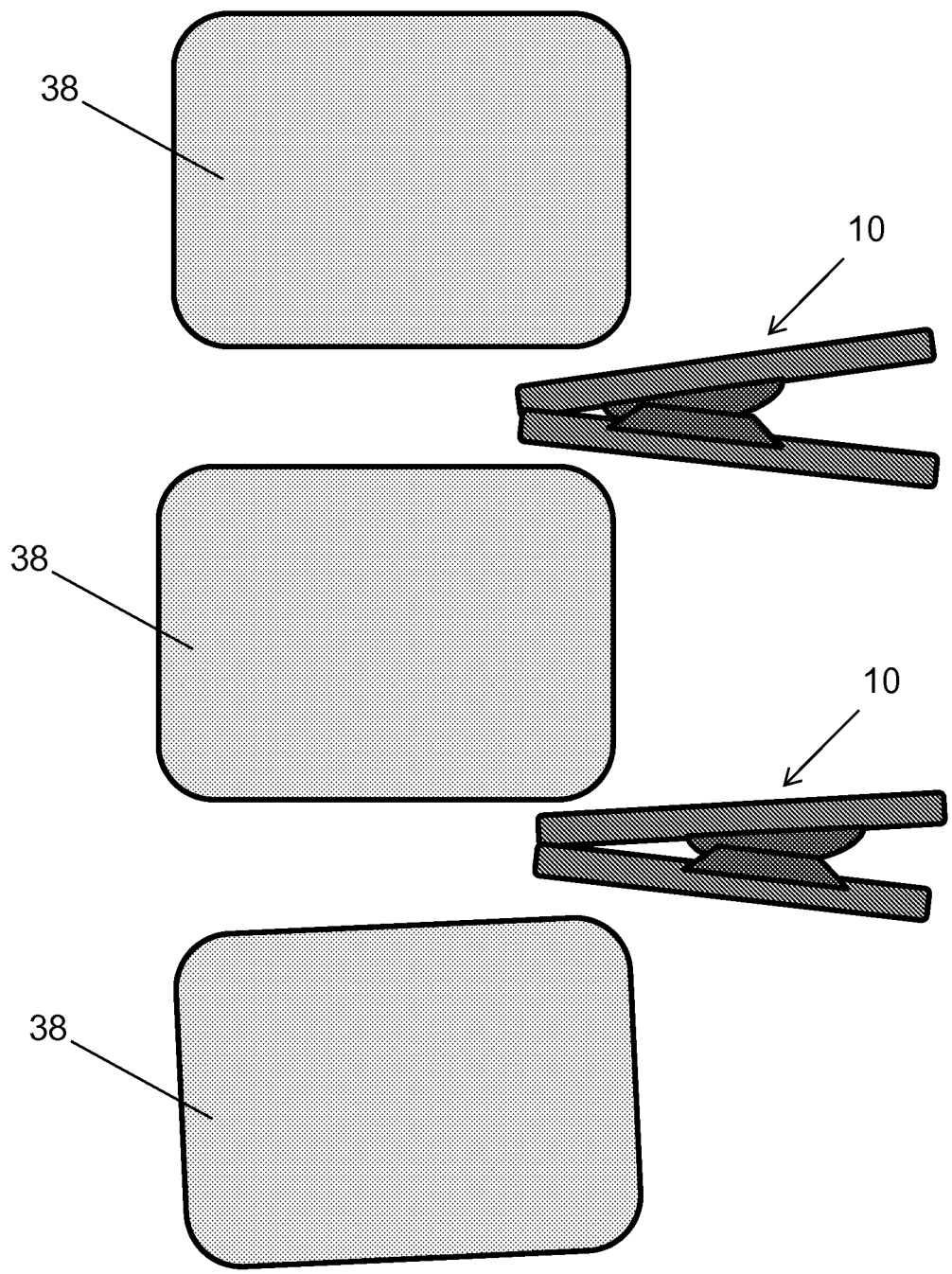
FIGS. 5A-5D depict the use of interbody spinal fusion cages as disclosed herein in a transforaminal lumbar interbody fusion procedure.

FIG. 5A illustrates several adjacent vertebrae 38. FIG. 5A also illustrates two interbody spinal fusion cages 10 approaching vertebrae 38 posteriorly. As seen in FIG. 5A, the anterior ends 16, 24 of superior member 12 and inferior member 14, respectively, are touching, which facilitates easy insertion of interbody spinal fusion cages 10 into the interbody spaces between adjacent vertebrae 38.

Figure 5B:
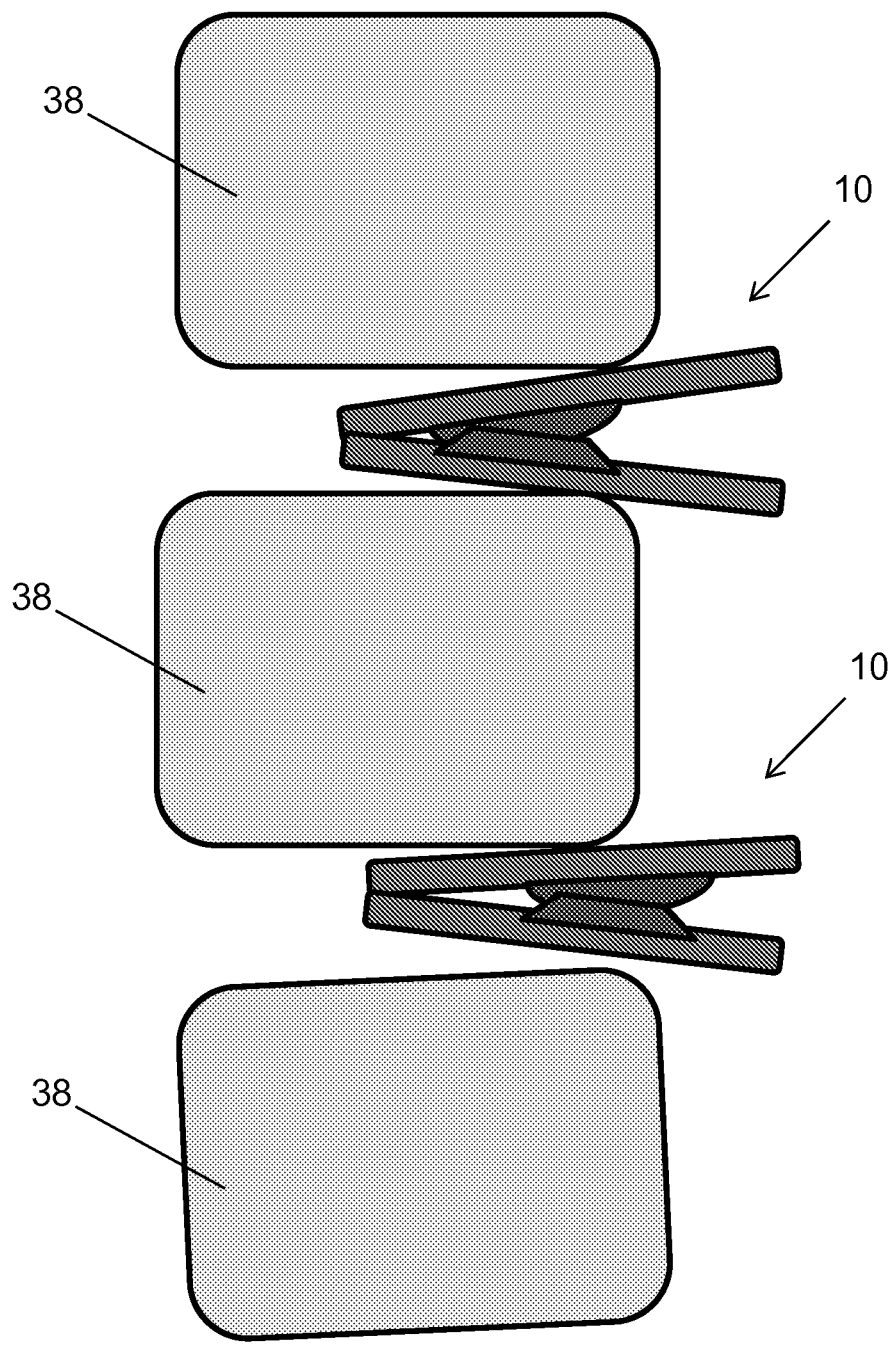
Figure 5C:
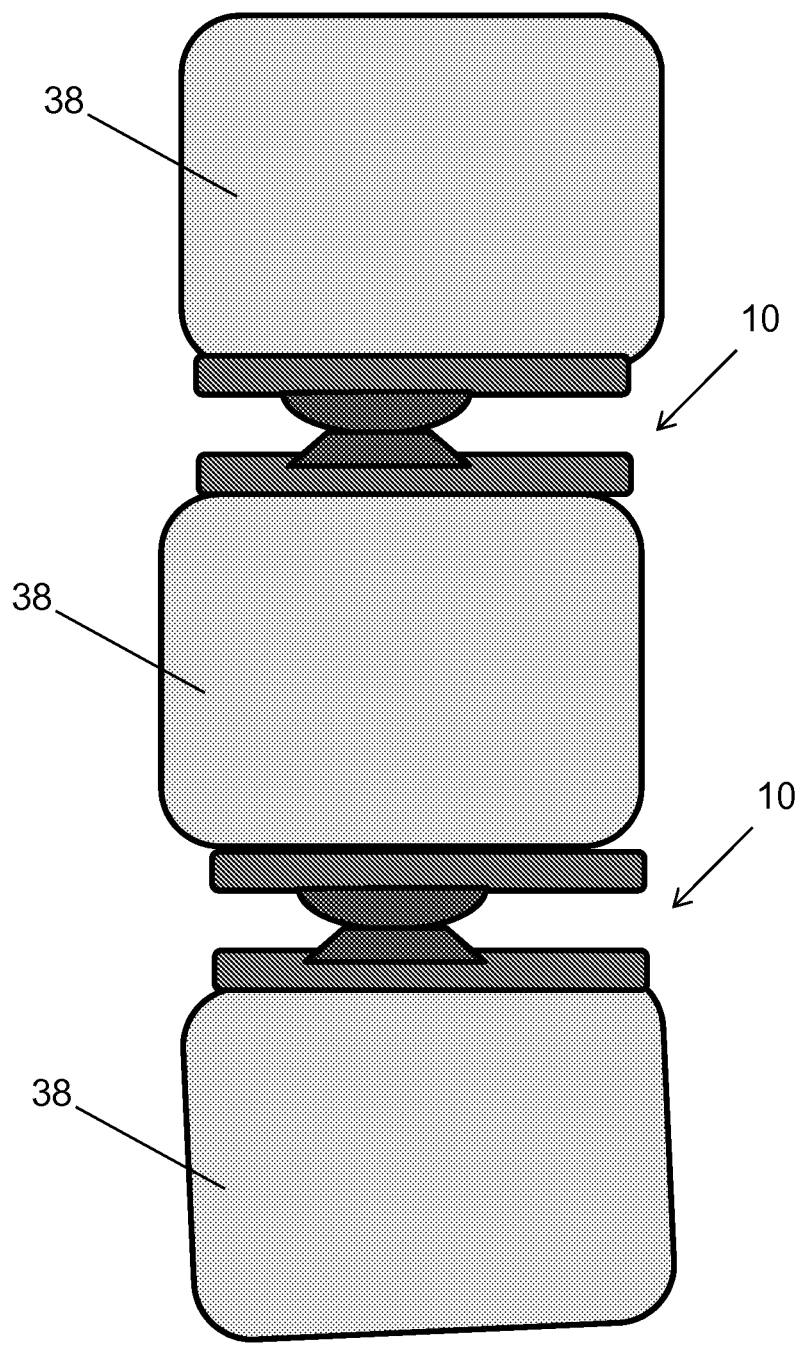

FIG. 5B shows interbody spinal fusion cages 10 having been advanced partially into the interbody spaces between adjacent vertebrae 38. FIG. 5C shows interbody spinal fusion cages 10 after they have been advanced fully into the interbody spaces between adjacent vertebrae 38. As shown in FIG. 5C, joint 32 permits anterior ends 16, 24 of superior member 12 and inferior member 14, respectively, to separate as interbody spinal fusion cages 10 move anteriorly.

Figure 5D:
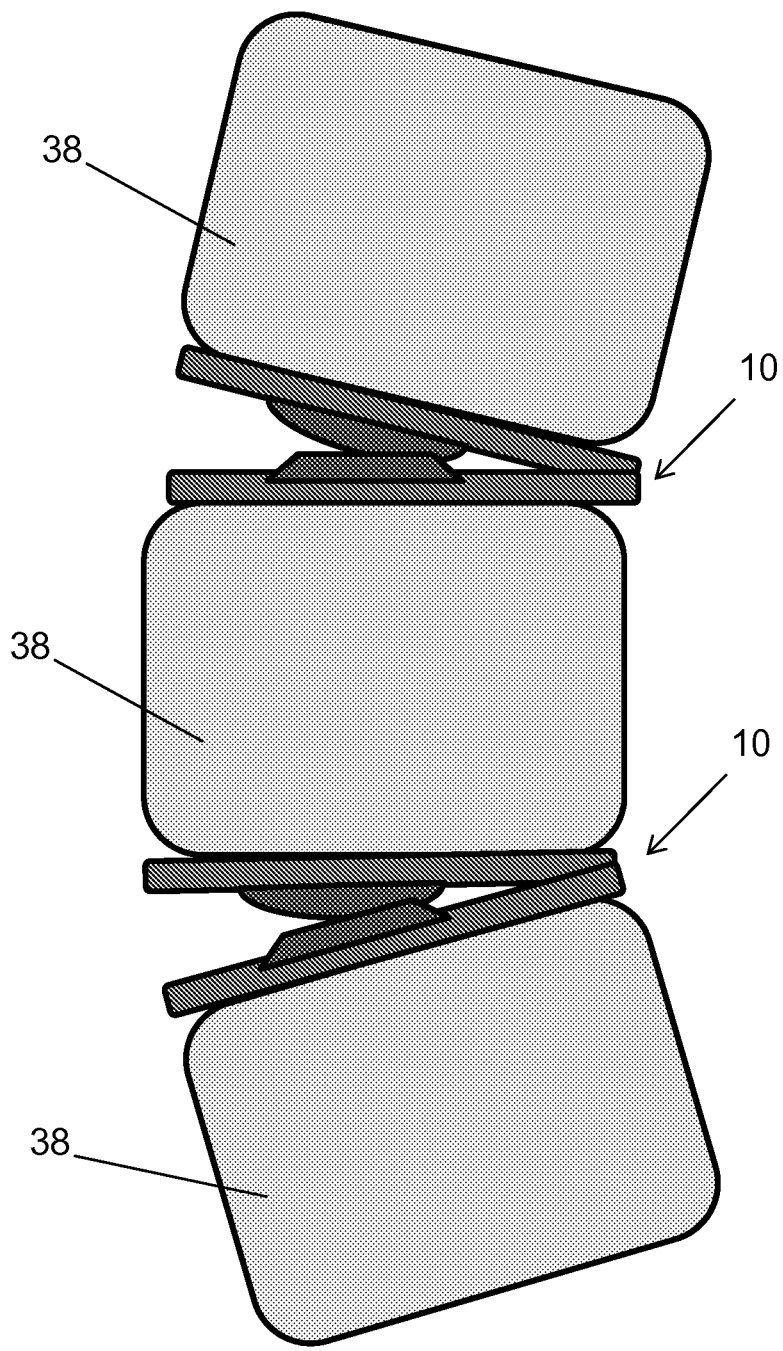

In FIG. 5D, posterior ends 18, 26 of superior member 12 and inferior member 14, respectively are touching, which places vertebrae 38 in lordosis.

It is desirable, however for posterior ends 18, 26 of superior member 12 and inferior member 14, respectively, not only to be touching, but also to be secured to one another such that the lordosis achieved in vertebrae 38 is not diminished or compromised over time. As shown in FIG. 1, superior member 12 can include a barbed tab 40 proximate posterior end 18, while inferior member 14 includes a complementary slot 42 proximate posterior end 26. Thus, when barbed tab 40 is inserted into slot 42 (see FIG. 1B), it cannot be removed without breaking the barbs off of tab 40. It is desirable for barbed tab 40 and slot 42 to be positioned somewhat anteriorly of posterior ends 18, 26 in order to minimize the risk of striking and breaking barbed tab 40 and/or slot 42 when placing interbody spinal fusion cage 10 between vertebrae 38.

In another embodiment, illustrated in FIGS. 3A-3C, interbody spinal fusion cage 10 includes a plurality of locking teeth 44 on superior member 12 and inferior member 14 proximate (and desirably somewhat anterior of) posterior ends 18, 26. Locking teeth 44 are configured to engage each other in a manner that prohibits posterior ends 18, 26 from separating from each other. FIG. 3B illustrates engagement between teeth 44 without lateral bending, while FIG. 3C illustrates engagement between teeth 44 with lateral bending.

Figure 6A:
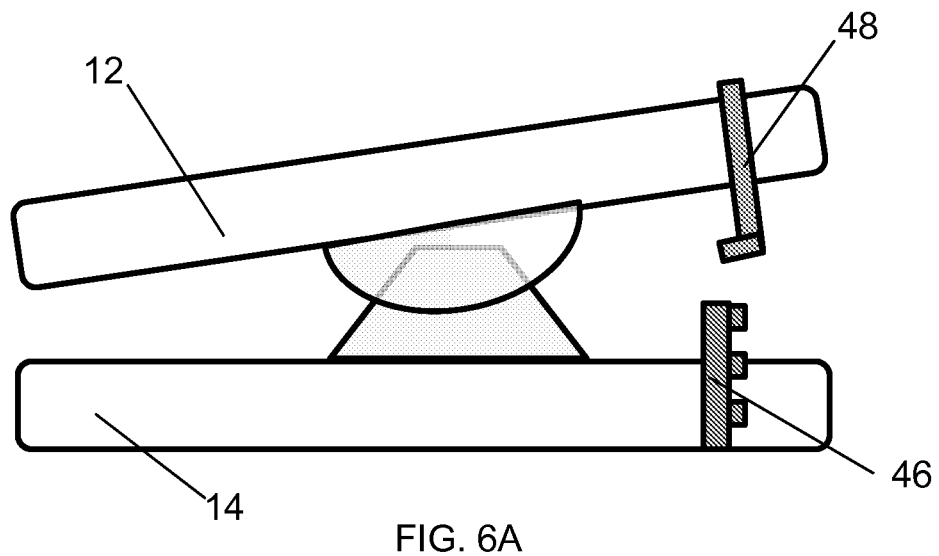
FIG. 6A is a side view schematic depiction of another embodiment of an interbody spinal fusion cage including a ratchet lock, with the superior and inferior members configured for insertion into an interbody space.
Figure 6B:
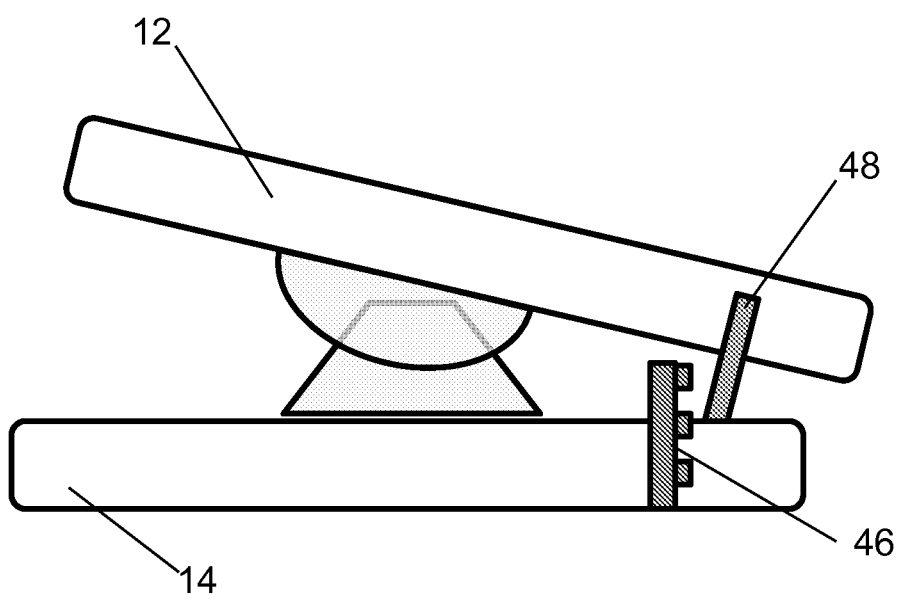
FIG. 6B is a side view schematic depiction of the interbody spinal fusion cage of FIG. 6A, with the superior and inferior members secured to each other via the ratchet lock.

Superior member 12 can also be secured to inferior member 14 via a ratchet lock mechanism, similar to a zip tie, such as shown in FIGS. 6A and 6B. As shown in FIGS. 6A and 6B, a ratchet 46 is attached to inferior member 14, while a pawl 48 is attached to superior member 12, though this arrangement could be reversed without departing from the spirit and scope of the instant disclosure. The ratchet and pawl configuration of FIGS. 6A and 6B provides the advantage that additional lordosis can be achieved over time by moving pawl 48 past an additional tooth on ratchet 46, but lordosis cannot be diminished or compromised because the ratchet lock only allows movement in one direction. It should also be understood that multiple ratchet locks, e.g., one on either side of axes 22, 30, can also be employed (e.g., replacing teeth 44, as illustrated in FIGS. 3A-3C, with ratchets and pawls).

Figure 7:
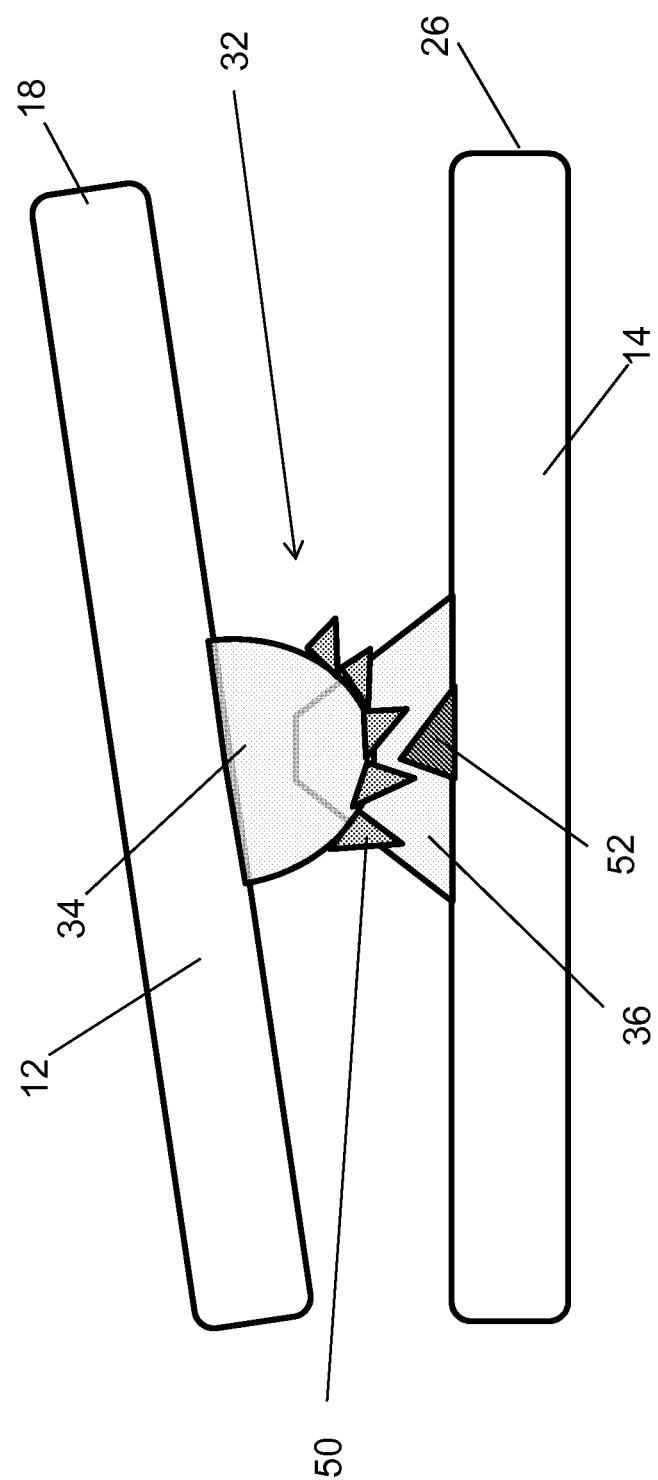
FIG. 7 is a side view schematic depiction of another embodiment of an interbody spinal fusion cage including a ratchet and pawl as part of the joint connecting the superior and inferior members.

In addition, a ratchet 50 and pawl 52 can be incorporated into joint 32, as shown schematically in FIG. 7. In FIG. 7, the teeth of ratchet 50 (five of which are shown, though it should be understood that any number of teeth can be used) are part of superior joint component 34, while pawl 52 is part of inferior joint component 36. The teeth are oriented in a manner that permits them to move freely past pawl 52 as posterior ends 18, 26 move towards each other, but that prevents them from moving past pawl 52 in a direction that would separate posterior ends 18, 26. This provides additional stability to the spinal lordosis achieved via the use of interbody spinal fusion cage 10.

Those of ordinary skill in the art will also be familiar with the use of graft material in the interbody space. In order to allow the graft to fuse to the adjacent vertebrae 38, each of superior member 12 and inferior member 14 can include a bone hole 56 through its respective bearing surface, as shown in FIG. 2.

Suitable materials for interbody spinal fusion cage 10 include, without limitation, titanium, poly ether ether ketone ("PEEK"), and other materials that are acceptable for permanent implantation into the human body. In certain embodiments, each of superior member 12 and inferior member 14 have an overall rectangular profile and dimensions of about 9 mm to about 14 mm wide, about 6 mm to about 17 mm high, and about 22 mm to about 34 mm long.

Although several embodiments have been described above with a certain degree of particularity, those skilled in the art could make numerous alterations to the disclosed embodiments without departing from the spirit or scope of this invention.

For example the various types of joint 32 disclosed herein can be used not only individually, but also in combination.

As another example, although certain embodiments are described with reference to a transforaminal lumbar interbody fusion procedure, the teachings herein could also be applied to good advantage in other procedures, including, without limitation, posterior lumbar interbody fusion procedures and interbody fusion from a posterior approach.

As a still further example, joint 32 can be moved closer to posterior ends 18, 26 or anterior ends 16, 24 to impart more or less mechanical advantage, to achieve more or less increase in anterior or posterior height, or to vary the degree to which the long axis of interbody spinal fusion cage 10 and joint 32 are offset relative to each other.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An interbody spinal fusion cage configured to achieve lordosis when placed posteriorly, the interbody spinal fusion cage comprising:
    a superior member including an anterior end, a posterior end, and a superior bearing surface extending along an axis between the anterior end of the superior member and the posterior end of the superior member;
    an inferior member including an anterior end, a posterior end, and an inferior bearing surface extending along an axis between the anterior end of the inferior member and the posterior end of the inferior member; and
    a hinge connected to the superior member at a first point between the anterior end of the superior member and the posterior end of the superior member and to the inferior member at a second point between the anterior end of the inferior member and the posterior end of the inferior member,
    wherein the hinge has a single axis of rotation that is oriented non-normal to the axis of the superior member and the axis of the inferior member, and that is fixed with respect to translation along the axis of the superior member and the axis of the inferior member, and
    wherein the hinge further comprises a ratchet and pawl.

2. The interbody spinal fusion cage according to claim 1, wherein the axis of rotation of the hinge forms an angle between 50 degrees and 80 degrees with respect to the axis of the superior member and the axis of the inferior member.

3. The interbody spinal fusion cage according to claim 1, wherein the superior member includes a superior bone hole through the superior bearing surface and wherein the inferior member includes an inferior bone hole through the inferior bearing surface.

4. The interbody spinal fusion cage according to claim 3, wherein:
the superior bone hole is located anterior of the first point, and
the inferior bone hole is located anterior of the second point.

5. The interbody spinal fusion cage according to claim 1, wherein:
the superior member includes a first ratchet element posterior of the first point,
wherein the inferior member includes a second ratchet element posterior of the second point, and
the first ratchet element and the second ratchet element are configured to allow the posterior end of the superior member and the posterior end of the inferior member to move towards each other and to prevent the posterior end of the superior member and the posterior end of the inferior member from moving apart from each other.

6. The interbody spinal fusion cage according to claim 5, wherein:
the superior member includes a third ratchet element posterior of the first point, the first ratchet element and the third ratchet elements being on opposing sides of the axis of the superior member,
the inferior member includes a fourth ratchet element posterior of the second point, the second ratchet element and the fourth ratchet element being on opposing sides of the axis of the inferior member, and
the third ratchet element and the fourth ratchet element are configured to allow the posterior end of the superior member and the posterior end of the inferior member to move towards each other and to prevent the posterior end of the superior member and the posterior end of the inferior member from moving apart from each other.

7. An interbody spinal fusion cage configured to achieve lordosis when placed posteriorly, the interbody spinal fusion cage comprising:
a superior member including an anterior end, a posterior end, a superior bearing surface extending between the anterior end of the superior member and the posterior end of the superior member, and a superior joint component between the anterior end of the superior member and the posterior end of the superior member; and
an inferior member including an anterior end, a posterior end, an inferior bearing surface extending between the anterior end of the inferior member and the posterior end of the inferior member, and an inferior joint component between the anterior end of the inferior member and the posterior end of the inferior member,
wherein the superior joint component is attached to the inferior joint component in a manner that allows the interbody spinal fusion cage to achieve lordosis even if implanted non-orthogonal to the sagittal plane,
wherein the superior joint component comprises a first hinge component and the inferior joint component comprises a second hinge component,
wherein the first and second hinge components together form a hinge having a single axis of rotation that is non-normal to a longitudinal axis of the interbody spinal fusion cage, and that is fixed with respect to translation along the longitudinal axis of the interbody spinal fusion cage, and
wherein:
the superior member includes first locking teeth proximate the posterior end of the superior member,
the inferior member includes second locking teeth proximate the posterior end of the inferior member, and
the first locking teeth are configured to engage the second locking teeth in a manner that prohibits the posterior end of the superior member from separating from the posterior end of the inferior member.

8. The interbody spinal fusion cage according to claim 7, wherein one of the first locking teeth and the second locking teeth comprises a ratchet and the other of the first locking teeth and the second locking teeth comprises a pawl.

9. The interbody spinal fusion cage according to claim 7, wherein:
the superior member comprises a superior bone hole through the superior bearing surface anterior of the superior joint component, and
the inferior member comprises an inferior bone hole through the inferior bearing surface anterior of the inferior joint component.

10. A method of performing a transforaminal lumbar interbody fusion, comprising:
inserting, via a posterior approach, an interbody spinal fusion cage between two vertebrae, the interbody spinal fusion cage comprising:
a superior member including an anterior end, a posterior end, and a superior bearing surface extending between the anterior end of the superior member and the posterior end of the superior member;
an inferior member including an anterior end, a posterior end, and an inferior bearing surface extending between the anterior end of the inferior member and the posterior end of the inferior member; and
a joint connecting the superior member to the inferior member in a manner that permits at least seesaw motion between the superior member and the inferior member about a single axis of rotation that is non-normal to a longitudinal axis of the interbody spinal fusion cage and that is fixed with respect to translation along the longitudinal axis of the interbody spinal fusion cage; and
securing the posterior end of the superior member to the posterior end of the inferior member, using a ratchet lock, in a lordotic configuration.

* * * * *